United States Patent [19]
Liu

[11] Patent Number: 5,997,568
[45] Date of Patent: Dec. 7, 1999

[54] ABSORBABLE POLYMER BLENDS AND SURGICAL ARTICLES FABRICATED THEREFROM

[75] Inventor: Cheng-Kung Liu, Glenside, Pa.

[73] Assignee: United States Surgical Corporation, Norwalk, Conn.

[21] Appl. No.: 08/784,503

[22] Filed: Jan. 17, 1997

Related U.S. Application Data

[60] Provisional application No. 60/010,268, Jan. 19, 1996.

[51] Int. Cl.[6] .................................................. A61B 17/04
[52] U.S. Cl. ......................... 606/228; 528/354; 525/415; 525/408
[58] Field of Search .................................. 606/228–230; 525/408, 415; 528/354, 357

[56] References Cited

U.S. PATENT DOCUMENTS

| | | | |
|---|---|---|---|
| 2,668,162 | 2/1954 | Lowe | 260/78.3 |
| 2,683,136 | 7/1954 | Higgins | 260/78.3 |
| 2,703,316 | 3/1955 | Scheider | 260/78.3 |
| 2,758,987 | 8/1956 | Salzberg | 260/78.3 |
| 3,169,945 | 2/1965 | Hostettler et al. | 260/78.3 |
| 3,225,766 | 12/1965 | Baptist et al. | 128/335.5 |
| 3,268,486 | 8/1966 | Klootwijk | 260/78.3 |
| 3,268,487 | 8/1966 | Klootwijk | 260/78.3 |
| 3,297,033 | 1/1967 | Schmitt et al. | 128/335.5 |
| 3,422,181 | 1/1969 | Chirgwin | 264/345 |
| 3,442,871 | 5/1969 | Schmitt et al. | 260/78.3 |
| 3,463,158 | 8/1969 | Schmitt et al. | 128/334 |
| 3,468,853 | 9/1969 | Schmitt et al. | 260/78.3 |
| 3,531,561 | 9/1970 | Trehu | 264/210 |
| 3,565,869 | 2/1971 | DeProspero | 260/78.3 |
| 3,597,449 | 8/1971 | DeProspero et al. | 260/340.2 |
| 3,620,218 | 11/1971 | Schmitt et al. | 128/334 R |
| 3,626,948 | 12/1971 | Glick et al. | 128/335.5 |
| 3,636,956 | 1/1972 | Schneider | 128/335.5 |
| 3,733,919 | 5/1973 | Rupp, II | 74/242.16 |
| 3,736,646 | 6/1973 | Schmitt et al. | 29/458 |
| 3,739,773 | 6/1973 | Schmitt et al. | 128/92 BC |
| 3,772,420 | 11/1973 | Glick et al. | 264/102 |
| 3,781,349 | 12/1973 | Ramsey et al. | 260/535 P |
| 3,784,585 | 1/1974 | Schmitt et al. | 260/861 |
| 3,792,010 | 2/1974 | Wasserman et al. | 260/32.2 R |
| 3,797,499 | 3/1974 | Schneider | 128/334 R |
| 3,839,297 | 10/1974 | Wasserman et al. | 260/78.3 R |
| 3,846,382 | 11/1974 | Ramsey et al. | 260/78.3 |
| 3,867,190 | 2/1975 | Schmitt et al. | 117/138.8 |
| 3,878,284 | 4/1975 | Schmitt et al. | 264/184 |
| 3,896,802 | 7/1975 | Williams | 128/156 |
| 3,902,497 | 9/1975 | Casey | 128/296 |
| 3,912,692 | 10/1975 | Casey et al. | 260/78.3 R |
| 3,937,223 | 2/1976 | Roth | 128/325 |
| 3,942,532 | 3/1976 | Hunter et al. | 128/335.5 |
| 3,982,543 | 9/1976 | Schmitt et al. | 128/335.5 |
| 3,987,937 | 10/1976 | Coucher | 222/193 |
| 4,033,938 | 7/1977 | Augurt et al. | 260/78.3 |
| 4,045,418 | 8/1977 | Sinclair | 260/78.3 |
| 4,052,988 | 10/1977 | Doddi et al. | 128/335.5 |
| 4,057,537 | 11/1977 | Sinclair | 260/78.3 R |
| 4,060,089 | 11/1977 | Noiles | 128/325 |
| 4,137,921 | 2/1979 | Okuzumi et al. | 128/335.5 |
| 4,157,437 | 6/1979 | Okuzumi et al. | 528/354 |

(List continued on next page.)

FOREIGN PATENT DOCUMENTS

| | | |
|---|---|---|
| 0117538 | 9/1984 | European Pat. Off. . |
| 0600237 | 6/1994 | European Pat. Off. . |
| 0654549 | 5/1995 | European Pat. Off. . |
| 779291 | 7/1957 | United Kingdom . |
| 1332505 | 10/1973 | United Kingdom . |
| 1414600 | 11/1975 | United Kingdom . |
| 2102827 | 2/1983 | United Kingdom . |
| 8404311 | 11/1984 | WIPO . |

*Primary Examiner*—Gary Jackson

[57] ABSTRACT

Bioabsorbable polymers and copolymers having accelerated mass loss, and more particularly bioabsorbable polymers and/or copolymers blended with particles of bioabsorbable polymers as well as surgical articles made totally or in part therefrom, including both monofilament and multifilament sutures, are provided.

21 Claims, 2 Drawing Sheets

U.S. PATENT DOCUMENTS

| | | | |
|---|---|---|---|
| 4,243,775 | 1/1981 | Rosensaft et al. | 525/415 |
| 4,246,904 | 1/1981 | Kaplan | 128/335.5 |
| 4,273,920 | 6/1981 | Nevin | 528/361 |
| 4,275,813 | 6/1981 | Noiles | 206/339 |
| 4,279,249 | 7/1981 | Vent et al. | 128/92 D |
| 4,300,565 | 11/1981 | Rosensaft et al. | 128/335.5 |
| 4,429,080 | 1/1984 | Casey et al. | 525/415 |
| 4,444,927 | 4/1984 | Borysko | 524/56 |
| 4,605,730 | 8/1986 | Shalaby et al. | 528/357 |
| 4,624,256 | 11/1986 | Messier et al. | 128/335.5 |
| 4,643,191 | 2/1987 | Bezwada et al. | 128/335.5 |
| 4,700,704 | 10/1987 | Jamiolkowski et al. | 128/335.5 |
| 4,744,365 | 5/1988 | Kaplan et al. | 128/335.5 |
| 4,788,979 | 12/1988 | Jarrett et al. | 128/335.5 |
| 4,791,929 | 12/1988 | Jarrett et al. | 128/335.5 |
| 4,891,263 | 1/1990 | Kotliar et al. | 428/225 |
| 4,916,193 | 4/1990 | Tang et al. | 525/413 |
| 4,920,203 | 4/1990 | Tang et al. | 525/409 |
| 4,965,300 | 10/1990 | Eichenauer et al. | 525/415 |
| 4,994,074 | 2/1991 | Bezwada et al. | 606/230 |
| 5,037,950 | 8/1991 | Bezwada et al. | 528/354 |
| 5,047,048 | 9/1991 | Bezwada et al. | 606/231 |
| 5,066,772 | 11/1991 | Tang et al. | 528/354 |
| 5,076,807 | 12/1991 | Bezwada et al. | 606/230 |
| 5,080,665 | 1/1992 | Jarrett et al. | 606/219 |
| 5,085,629 | 2/1992 | Goldberg et al. | 604/8 |
| 5,100,433 | 3/1992 | Bezwada et al. | 606/230 |
| 5,116,932 | 5/1992 | Fujiwa | 528/80 |
| 5,120,802 | 6/1992 | Mares et al. | 525/415 |
| 5,145,945 | 9/1992 | Tang et al. | 528/370 |
| 5,147,399 | 9/1992 | Dellon et al. | 623/12 |
| 5,152,781 | 10/1992 | Tang et al. | 606/230 |
| 5,185,408 | 2/1993 | Tang et al. | 525/415 |
| 5,210,108 | 5/1993 | Spinu et al. | 521/182 |
| 5,225,520 | 7/1993 | Kennedy et al. | 528/354 |
| 5,225,521 | 7/1993 | Spinu | 528/354 |
| 5,236,444 | 8/1993 | Muth et al. | 606/230 |
| 5,252,701 | 10/1993 | Jarrett et al. | 528/354 |
| 5,278,202 | 1/1994 | Dunn et al. | 523/113 |
| 5,314,989 | 5/1994 | Kennedy et al. | 528/354 |
| 5,322,925 | 6/1994 | Muth et al. | 528/354 |
| 5,352,515 | 10/1994 | Jarrett et al. | 428/357 |
| 5,391,707 | 2/1995 | Jiang | 528/354 |
| 5,399,666 | 3/1995 | Ford | 528/354 |
| 5,403,347 | 4/1995 | Roby et al. | 606/354 |
| 5,543,218 | 8/1996 | Bennett et al. | 428/375 |

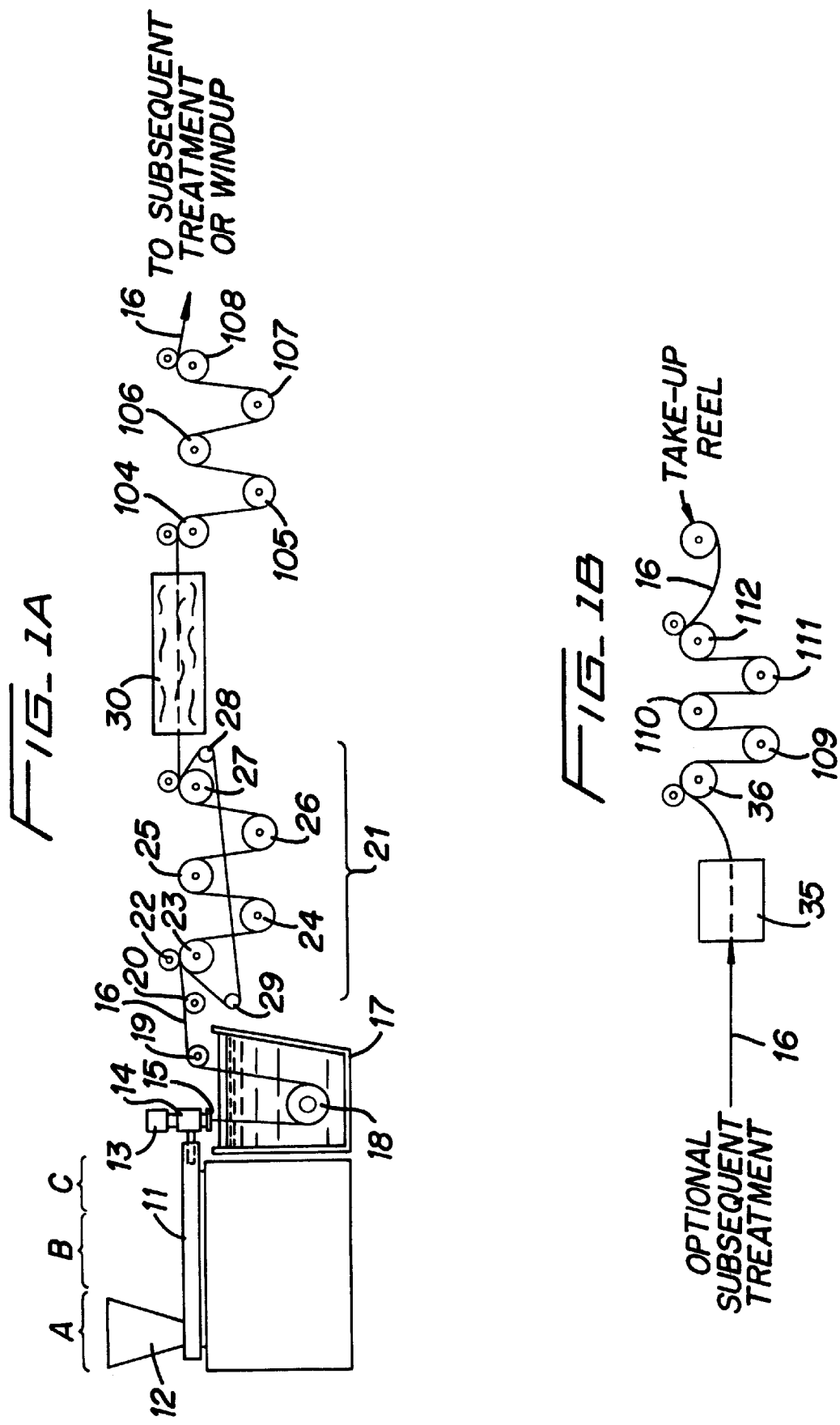

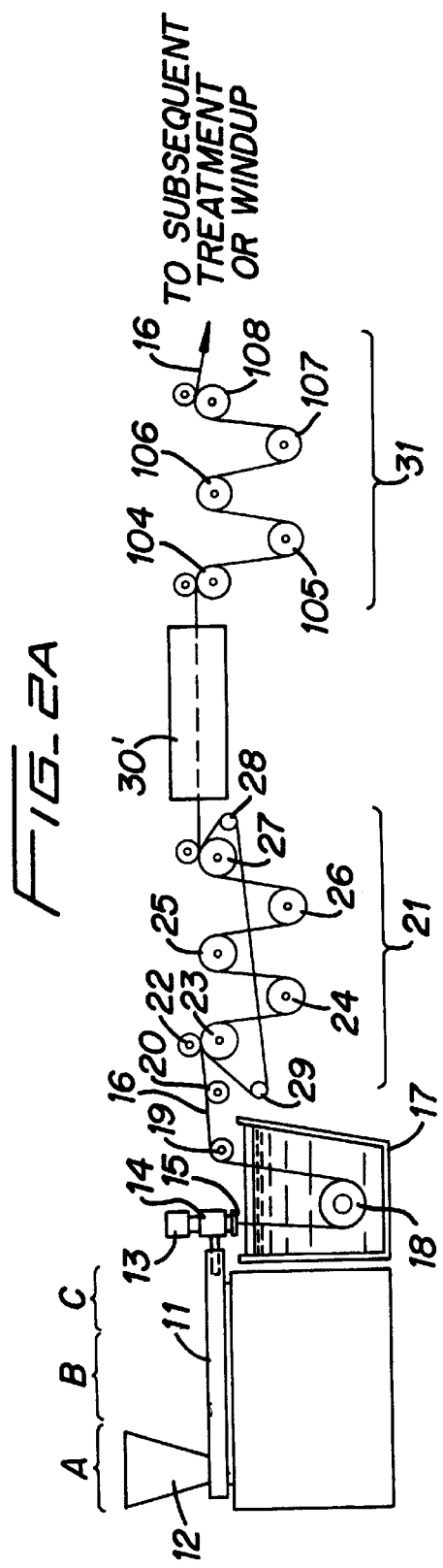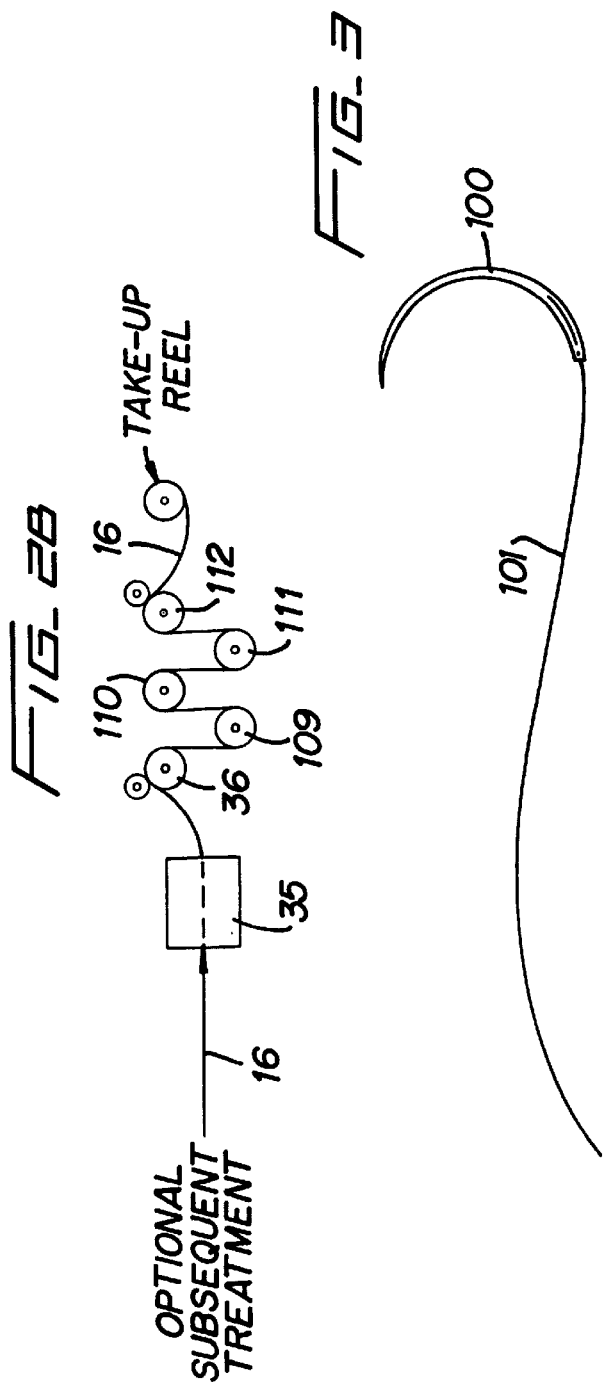

ABSORBABLE POLYMER BLENDS AND SURGICAL ARTICLES FABRICATED THEREFROM

This application claims benefit of provisional application 60/010,268 filed on Jan. 19, 1996.

TECHNICAL FIELD

Bioabsorbable polymer blends having accelerated mass loss, and more particularly bioabsorbable polymers and/or copolymers blended with particles of bioabsorbable polymers as well as surgical articles made totally or in part therefrom, including both monofilament and multifilament sutures, are provided.

BACKGROUND OF THE INVENTION

Polymers and copolymers of, and surgical devices made from lactide and/or glycolide and/or related compounds are well-know. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for use in surgery-polyglycolic/poly (lactic acid) homo-and copolymers: 1, *"Polymer*, Volume 20, pages 1459–1464 (1979), and D. F. Williams (ed.) *Biocompatibility Of Clinical Implant Materials*, Volume II, chapter 9: "Biodegradable Polymers" (1981).

U.S. Pat. No. 4,052,988 describes random copolymers containing dioxanone and up to 50 percent by weight of other copolymerizable monomers which produce non-toxic and absorbable copolymers.

As described above, bioabsorbable surgical devices, such as surgical sutures, are known in the art. A desirable characteristic of bioabsorbable devices, such as sutures, is their ability to exhibit and maintain desired tensile properties for a predetermined time period followed by rapid absorption of the mass of the surgical device (hereinafter "mass loss").

Absorbable multifilament sutures such as Dexon, Vicryl, and Polysorb commercially available from Davis & Geck (Danbury, Connecticut), Ethicon, Inc. (Sommerville, N.J.), and United States Surgical Corporation (Norwalk, Conn.), respectively, are known in the industry as short term absorbable sutures. The classification short term absorbable sutures generally refers to surgical sutures which retain about 20 percent of their original strength at three weeks after implantation, with the suture mass being essentially absorbed in the body within about 60 to 90 days post implantation.

Long term absorbable sutures are generally known to be sutures which retain about 20 percent of their original strength at six or more weeks after implantation, with the suture mass being essentially absorbed in the body within about 180 days post implantation. For example, PDS II, a synthetic absorbable monofilament suture, commercially available from Ethicon, Inc. (Sommerville, N.J.), retains about 20 to about 30 percent of its original strength at six weeks after implantation. However, PDS II exhibits minimal mass loss until 90 days after implantation with the suture mass being essentially absorbed in the body about 180 days after implantation. Maxon, commercially available from Davis & Geck (Danbury, Conn.) is another absorbable synthetic monofilament generally fitting this absorption profile.

Therefore, it would be advantageous to provide bioabsorbable surgical devices which exhibit and maintain tensile properties for the desired period of time while having a shorter and thus improved mass loss profile, such as a long term bioabsorbable synthetic monofilament surgical suture having tensile properties and handling characteristics comparable to PDS II, which exhibits a shorter mass loss profile.

U.S. Pat. No. 4,444,927 describes a process for fabricating dioxanone articles by heating a mixture of polydioxanone and finely divided sucrose or lactose nucleating agent. The '927 patent teaches that as a result of the presence of nucleating agents, the cycling time of injection molding of the polymers can be significantly reduced in many cases. However, the '937 patent does not disclose or suggest that such blends would reduce the mass loss absorption time, let alone disclose blending fine particles of fast absorbing polymers with longer term absorbable polymers to reduce the mass loss time of the longer term absorbable polymers.

SUMMARY OF THE INVENTION

It has now been found that absorbable surgical articles having improved mass loss profiles may be formed from blends of bioabsorbable polymers and fine particles of bioabsorbable polymers having a melting point higher than the bioabsorbable polymers blended therewith. Suitable bioabsorbable polymers include homopolymers and copolymers of lactide, caprolactone, dioxanone, trimethylene carbonate, with dioxanone being preferred. Suitable fine bioabsorbable polymer particles include polylactide, polyglycolide, and copolymers thereof.

Preferably, blends useful in forming surgical articles include from about 0.01 to about 1 percent by weight of fine polymer particles with about 0.05 to about 0.5 percent by weight being preferred; the remainder being bioabsorbable polymer.

In a particularly useful embodiment the blends may be spun into fibers. The fibers can be fabricated into both monofilament and braided multifilament sutures.

BRIEF DESCRIPTION OF THE DRAWINGS

FIGS. 1A and 1B are a schematic illustration of an apparatus which is suitable for manufacturing the monofilament suture of this invention; and, FIGS. 2A and 2B are a modification of the apparatus of FIG. 1A which is particularly suitable for manufacturing the monofilament sutures of the present invention of smaller size, e.g., sizes 3/0 and smaller.

FIG. 3 is a perspective view of a suture of the present invention attached to a needle.

DESCRIPTION OF THE PREFERRED EMBODIMENTS

It has been found that fine bioabsorbable particles such as fine particles of polyglycolide and/or copolymers of glycolide and lactide advantageously be blended with other bioabsorbable polymers, such as polydioxanone, polylactide, polycaprolactone, polytrimethylene carbonate, etc. to form a bioabsorbable polymeric blend useful in forming surgical articles, such as surgical sutures, which exhibit an increase mass loss profile as discussed hereinabove.

Such bioabsorbable blends include from about 99 to about 99.99 weight percent bioabsorbable polymer, the remainder being bioabsorbable fine polymer particles.

Suitable bioabsorbable fine polymer particles include polyglycolide as well as copolymers of glycolide and lactide particles that have a particle size of about 0.05 to about 5 microns with 0.1 to about 1 microns being preferred.

Such particles can be fabricated by processing polyglycolide or copolymers of glycolide and lactide (commercially available from Boehinger Ingelheim) through a Micro-Mill® machine (commercially available from Bel and Art Products).

It is believed that when fine polymer particles, such as polyglycolide and/or copolymers of glycolide and lactide are blended with a bioabsorbable polymer, such as polydioxanone; the fine polymer particles act as nucleating agents during subsequent fiber processing (described herein below). For example, the resultant crystalline domain of polydioxanone fibers will have polyglycolide fine particles embedded therein. It is believed that this impurity will enhance the rate of mass loss without impacting on the tensile properties, handling characteristics, and/or strength retention of the suture.

Although it is preferred to fabricate surgical sutures from the disclosed copolymers, a wide variety of surgical articles can be manufactured from the copolymer of the present invention. These include but are not limited to clips and other fasteners, staples, sutures, pins, screws, prosthetic devices, wound dressings, drug delivery devices, anastomosis rings, and other implantable devices. Fibers made from the copolymers of this invention can be knitted or woven with other fibers, either absorbable or nonabsorbable to form meshes or fabrics. The compositions of this invention can also be used as an absorbable coating for surgical devices. Surgical articles can be formed from the copolymers using any know technique, such as, for example, extrusion, molding and/or solvent casting. The copolymers can be used alone, blended with other absorbable compositions, or in combination with non-absorbable components.

Multifilament sutures of the present invention may be made by methods known in the art. Braid constructions such as those disclosed and claimed in U.S. Pat. Nos. 5,059,213 and 5,019,093 are suitable for multifilament sutures herein.

A suitable process for the manufacture of monofilament sutures comprises the operations of melt extruding the resin at an extrusion temperature of from about 90° C. to about 200° C. to provide a monofilament, stretching the solidified monofilament at a temperature of from about 30° C. to about 60° C. in water (or other suitable liquid medium) or at from about 25° C. to about 95° C. in air (or other suitable gaseous medium) at a stretch ratio of from about 3:1 to about 10:1 to provide a stretched monofilament. Optionally, the stretched monofilament may be stretched again in air or other suitable gaseous medium preferably at 1.05:1 to about 1.40:1. The suture may then be annealed at a temperature of from about 40° C. to about 100° C. to provide the finished suture.

FIG. 1A schematically illustrates a monofilament suture manufacturing operation which is especially suitable for producing larger size sutures, e.g., those of sizes 2/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of the bioabsorbable polymer and fine bioabsorbable polymer particles can be introduced to the extruder through hopper 12. Optionally the fine bioabsorbable polymer particles can be blended with the bioabsorbable polymer prior to placement in the hopper.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 10 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 80° C. to 110° C., zone B at from about 100° C. to 190° C. and zone C at from about 120° C. to about 200° C. Additional temperature parameters include: metering pump block 13 at from about 120° C. to about 180° C., spin pack 14 at from about 120° C. to about 180° C., spinneret 15 at from about 120° C. to about 180° C. and quench bath at from about 15° C. to about 60° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament enters first godet station 21.

First godet station 21 is equipped with five individual godets around which monofilament 16 is wrapped. First godet 23 is provided with nip roll 22 to prevent slippage which might otherwise result. Upon entering first godet station 21, monofilament 16 passes over first godet 23, under second godet 24, over third godet 25, under fourth godet 26 and over fifth godet 27. Fifth godet 27 is proximally located to separation roller 28 which is provided with a plurality of laterally spaced circumferential grooves which act as guides for monofilament 16. After monofilament 16 passes over fifth godet 27 it wraps around a groove on separation roller 29 located proximal to first godet station 23. Monofilament 16 wraps around separation roller 29, ascends up to first godet 23 and continues onward to the remaining godets in the manner just described. When the monofilament passes over the fifth godet 27 a second time, it may be wrapped around a second groove on separation roller 28. The monofilament then extends back to separation roller 29 and around a corresponding groove thereon. The monofilament may pass through first godet station 21 any desired number of times. The solidified monofilament is thus allowed to dwell at ambient conditions before the monofilament enters heating unit 30. In this fashion monofilament 16 is aged or exposed to ambient conditions for a desired period of time prior to being stretched.

It is to be understood that aging or exposing the monofilament to ambient conditions for a predetermined period of time prior to drawing the monofilament can be accomplished in many different ways. For example, any number of godets may be employed to provide the dwell period. In addition, the arrangement of the godets can be varied. Also, other structures suitable for providing aging of the monofilament prior to stretching will be apparent to those skilled in the art.

Monofilament 16 passing from godet 27 is stretched, e.g., with stretch ratios on the order of from about 2:1 to about 8:1 and preferably from about 3:1 to about 6:1, to effect its orientation and thereby increase its tensile strength.

In the stretching operation shown in FIG. 1A, generally suitable for larger size sutures, e.g., sizes 2 to 2/0, monofilament 16 is drawn through hot water (or other suitable liquid medium) draw bath 30 by means of godets 104, 105, 106, 107 and 108 or any other suitable arrangement of godets which rotate at a higher speed than godet station 21 to provide the desired stretch ratio. The temperature of hot water draw bath 30 is advantageously from about 30° C. to about 65° C. and preferably is from about 40° C. to about 55° C.

In an alternative stretching operation shown in FIG. 1B, generally preferred for smaller sutures sizes, e.g., sizes 3/0 to 8/0, monofilament 16 is drawn by godets 104, 105, 106, 107, and 108 or any other suitable godet arrangement through hot air convection oven chamber 30' at a temperature of from about 25° C. to about 95° C. and preferably from about 40° C. to about 75° C. to provide the desired amount of stretch.

Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 36, 109, 110, 111, and 112 or any other suitable godet arrangement through second hot air oven chamber 35 at a temperature of from about 40° C. to about 95° C. and preferably from about 50° C. to about 85° C. During the relaxation process, at these temperatures, monofilament 16 will generally recover to within about 80 to about 98 percent, and preferably to within about 90 percent, of its pre-annealed length to provide the finished suture. For relaxation, the third godet station rotates at a slower speed than the second godet station, thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 40° C. to about 95° C., as described in U.S. Pat. No. 3,630,205. After a suitable period of residency in the heating cabinet, e.g., about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

The suture of the present invention, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the present invention, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

In order that those skilled in the art may be better able to practice the present invention, the following examples are given as an illustration of the preparation of copolymers described herein as well as of the preparation and superior characteristics of the sutures described herein. It should be noted that the invention is not limited to the specific details embodied in the examples.

EXAMPLE 1

Polyglycolide pellets (100 grams) are ground in a Micro-Mill® machine (commercially available from Bel-Art Products for 30 minutes, until the resultant polymer particles have a particle size of 0.5 micron.

EXAMPLE 2

The fine particles of polyglycolide of Example 1 (5 grams) and 1,4 dioxane-2-one (5000 grams) are added to a reactor. The mixture is blended at 100° C., with stirring under a nitrogen atmosphere for 24 hours. The polyglycolide/poly 1,4 dioxane-2-one blend was then sampled.

The reaction product was isolated, comminuted, and treated to remove residual reactants using known techniques. The polymer was then heated under vacuum to remove residual water, residual solvent, and/or unreacted monomer.

EXAMPLE 3

Table I below sets forth typical conditions for extruding, stretching an annealing size 3/0 of sutures. The monofilament sutures are fabricated from the resin of Example 1.

TABLE I

CONDITIONS OF MANUFACTURING OF MONOFILAMENTS

|  | Example 2 Resin |
| --- | --- |
| Suture Size | 3/0 |
| Process Conditions | |
| extruder screw, rpm | 1.5 |
| pump rpm | 11 |
| barrel temp., ° C., zone A | 100 |
| barrel temp., ° C., zone B | 130 |
| barrel temp., ° C., zone C | 135 |
| clamp temp., ° C. | 135 |
| adapter temp., ° C. | 135 |
| pump temp., ° C. | 135 |
| spinneret temp., ° C. | 135 |
| barrel melt temp., ° C. | 130 |
| pump melt temp., ° C. | 132 |
| spinneret melt temp., ° C. | 132 |
| barrel pressure, psi | 1800 |
| pump pressure, psi | 500 |
| spinneret pressure, psi | 2600 |
| pump size, cc per revolution | 0.16 |
| diameter of spinneret, orifices, mm | 1.25 |
| no. of spinneret orifices | 1 |
| quench bath temp., ° C. | 2.0 |
| Process Conditions | Stretching (Orienting) Operation |
| oven temp., ° C. | 50 |
| first godet, mpm | 4 |
| second godet, mpm | 20 |
| second oven temp., ° C. | 90 |
| third godet, mpm | 26 |
| draw ratio | 6.5:1 |
| Process Conditions | Annealing Operation |
| oven temp., ° C. | 85 |
| time (hrs.) | 18 |
| relaxation (%) | 5 |

EXAMPLE 4

The fine particles of polyglycolide of Example 1 (5 grams) and 1,4 dioxane-2-one (5000 grams) are added directly to the hopper of a monofilament extruder (commercially available from J. J. Jenkins, Inc.). The polyglycolide particles and 1,4 dioxane-2-one are extruded, stretched and annealed under conditions set forth in Table I above to form a suture.

It will be understood that various methods may be made to the embodiments disclosed herein. Therefore, the above description should not be construed as limiting, but merely as exemplifications of preferred embodiments. Those skilled in the art will envision other modifications within the scope and spirit of the claim appended hereto.

We claim:

1. A composition comprising:
   a blend of bioabsorbable polymers containing a first bioabsorbable polymer and a second bioabsorbable polymer, the first bioabsorbable polymer having a particle size in the range of about 0.05 to 5 microns.

2. A composition as in claim 1 wherein the first bioabsorbable polymer has a melting point higher than the melting point of the second bioasorable polymer.

3. A composition as in claim 1 wherein the first bioabsorbable polymer is selected from the group consisting of polylactide, polyglycolide and polylactide-co-glycolide.

4. A composition as in claim 1 wherein the second bioabsorbable polymer is selected from the group consisting of polymers of lactide, caprolactone, dioxanone and trimethylene carbonate.

5. A composition as in claim 1 wherein the first bioabsorbable polymer has a particle size in the range of about 0.1 to about 1 micron.

6. A composition as in claim 1 wherein the first bioabsorbable polymer comprises about 0.01 to about 1 percent by weight of the composition.

7. A composition as in claim 1 wherein the first bioabsorbable polymer comprises about 0.05 to about 0.5 percent by weight of the composition.

8. A suture fabricated from the composition of claim 1.

9. A surgical device comprising
   a fiber made from a first bioabsorbable polymer blended with a second bioabsorbable polymer, the first bioabsorbable polymer having a particle size in the range of about 0.05 to about 5 microns.

10. A surgical device as in claim 9 wherein the first bioabsorbable polymer has a melting point higher than the melting point of the second bioabsorbable polymer.

11. A surgical device as in claim 9 wherein the first bioabsorbable polymer is selected from the group consisting of polylactide, polyglycolide and polylactide-co-glycolide.

12. A surgical device as in claim 9 wherein the second bioabsorbable polymer is selected from the group consisting of polymers of lactide, caprolactone, dioxanone and trimethylene carbonate.

13. A surgical device as in claim 9 wherein the first bioabsorbable polymer has a particle size in the range of about 0.1 to about 1 micron.

14. A surgical device as in claim 9 wherein the first bioabsorbable polymer comprises about 0.01 to about 1 percent by weight of the composition.

15. A surgical device as in claim 9 wherein the first bioabsorbable polymer comprises about 0.05 to about 0.5 percent by weight of the composition.

16. A method of making a surgical device comprising:
   preparing a composition containing a mixture of a first absorbable polymer having a first melting point and a particle size in the range of about 0.5 to about 5 microns, and a second bioabsorbable polymer having a melting point below the melting point of the first bioabsorbable polymer;
   heating the composition to a temperature above the melting point of the second absorbable polymer but below the melting point of the first absorbable polymer; and
   shaping the treated composition to form a surgical device; and
   cooling the composition.

17. A method as in claim 16 wherein the shaping step comprises extruding the composition to form a filament.

18. A method as in claim 16 wherein the step of preparing a composition comprises mixing a first bioabsorbable polymer having a particle size in the range of about 0.1 to about 1 micron with pellets of a second bioabsorbable polymer.

19. A method as in claim 16 wherein the step of preparing a composition comprises adding the first absorbable polymer to the second bioabsorbable polymer to produce a mixture containing about 0.01 to about 1 percent by weight of the first bioabsorbable polymer.

20. A method as in claim 16 wherein the first bioabsorbable polymer is selected from the group consisting of polylactide, polyglycolide and polylactide-co-glycolide and the second bioabsorbable polymer is selected from the group consisting of homo- and copolymers of lactide, caprolactone, dioxanone, and trimethylene carbonate.

21. A suture prepared in accordance with the method of claim 16.

* * * * *